(12) United States Patent
Quintana et al.

(10) Patent No.: US 12,718,955 B2
(45) Date of Patent: Aug. 25, 2026

(54) AUTOMATIC CAD MODEL SELECTION SYSTEM AND METHOD FOR RADIOGRAPHY IMAGING SYSTEMS

(71) Applicant: GE Precision Healthcare LLC, Wauwatosa, WI (US)

(72) Inventors: Gonzalo Iñaki Quintana, Montrouge (FR); Pablo Milioni de Carvalho, Chaville (FR); Laurence Vancamberg, Poissy (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 439 days.

(21) Appl. No.: 18/216,266

(22) Filed: Jun. 29, 2023

(65) Prior Publication Data

US 2025/0006381 A1 Jan. 2, 2025

(51) Int. Cl.

| | |
|---|---|
| ***G06K 9/00*** | (2022.01) |
| ***G06T 7/00*** | (2017.01) |
| ***G06V 10/44*** | (2022.01) |
| ***G06V 10/74*** | (2022.01) |
| ***G16H 30/20*** | (2018.01) |
| ***G16H 50/20*** | (2018.01) |
| ***G16H 50/50*** | (2018.01) |

(52) U.S. Cl.

CPC ........... *G16H 50/50* (2018.01); *G06T 7/0012* (2013.01); *G06V 10/44* (2022.01); *G06V 10/761* (2022.01); *G16H 30/20* (2018.01); *G16H 50/20* (2018.01); *G06T 2207/20081* (2013.01)

(58) Field of Classification Search

None

See application file for complete search history.

(56) References Cited

U.S. PATENT DOCUMENTS

| | | | | |
|---|---|---|---|---|
| 10,417,528 B2 | 9/2019 | Ma et al. | | |
| 2021/0090694 A1* | 3/2021 | Colley | .................. | G16B 30/00 |
| 2021/0264025 A1 | 8/2021 | Givental et al. | | |

(Continued)

FOREIGN PATENT DOCUMENTS

| | | | | |
|---|---|---|---|---|
| TW | 1703458 B * | 9/2020 | ......... | G06F 18/2415 |
| WO | WO-2022272147 A9 * | 4/2023 | ............ | G10L 15/26 |

OTHER PUBLICATIONS

EP application 24181834.3 filed Jun. 12, 2024—extended Search Report issued Dec. 2, 2024; 10 pages.

*Primary Examiner* — Wei Wen Yang

(74) *Attorney, Agent, or Firm* — Boyle Fredrickson, S.C.

(57) ABSTRACT

A system and method for the determination of a data analysis model to be employed on a data analysis system using an evaluation dataset obtained from the data analysis system. The data analysis models are trained in a suitable manner, such as via a federated learning system, to each include various training features. The evaluation dataset is run through each of the data analysis models to extract features from the evaluation dataset for comparison with the training features of each data analysis model to determine the similarity of the training features of the data analysis models to the extracted features. The results of the comparison are presented for review and validation of the selected data analysis model(s). Further, the extraction of the features from the evaluation dataset can be performed on raw data from the data analysis system, or a combination of raw data and annotated data.

19 Claims, 6 Drawing Sheets

(56) References Cited

U.S. PATENT DOCUMENTS

| | | | | |
|---|---|---|---|---|
| 2022/0012872 | A1 * | 1/2022 | Gilboa-Solomon | ......................... G06F 16/9536 |
| 2022/0028551 | A1 | 1/2022 | Jordan | |
| 2022/0108177 | A1 | 4/2022 | Samek et al. | |
| 2022/0180514 | A1 | 6/2022 | Vlasimsky | |

* cited by examiner

AUTOMATIC CAD MODEL SELECTION SYSTEM AND METHOD FOR RADIOGRAPHY IMAGING SYSTEMS

BACKGROUND OF DISCLOSURE

The present invention generally relates to a system and method for improved workflow of a medical imaging system. Particularly, the present invention relates to an automatic system and method for selecting an optimal computer algorithm for processing medical images.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of objects in an object. The information gained from medical diagnostic imaging has applications in many fields, including medicine and manufacturing.

An example of a medical diagnostic imaging system is Picture Archival Communication Systems (PACS). PACS is a term for equipment and software that permits images, such as x-rays, ultrasound, CT, MRI, EBT, MR, or nuclear medicine for example, to be electronically acquired, such as by using an imaging device having the desired modality for the image to be acquired, e.g., a radiography imaging device, stored and transmitted for viewing. Images from an exam may be viewed immediately or stored, or transmitted. The images may be viewed on diagnostic workstations by users, for example radiologists. In addition to viewing the images, the user may also view patient information associated with the image for example the name of the patient or the patient's sex.

Many PACS systems run computer software for executing computer assisted classification, detection and/or diagnosis (CAD) tasks. In the execution of these tasks, the computer software constituting the CAD systems generally relies on, for example, anatomical structures, clinical purpose, and function, among other variables. The CAD systems employed with the various imaging systems also account for other variables such as image acquisition protocols, including modality, reconstruction algorithms, and contrast agents, for example.

In the development of the these CAD systems, the CAD systems are constructed to generate results for numerous specific conditions. Developers designing algorithms to meet specific conditions generally account for most variations in the acquisition protocols. Typical variations may include reconstruction methods, noise in the data, temporal resolution, image contrast employed, and other variables. However, once designed, the algorithm/CAD system must be trained on suitable training datasets in order to enable the CAD system produce accurate results regarding the detection of anomalies within the images supplied to the CAD system.

In order to train these CAD systems for instantiation and use on various imaging systems, a federated learning process can be employed, as shown schematically in FIG. 1. In federated learning, a global or general CAD system 1100 is developed, which is more cost effective in regards to its development than development of a targeted CAD system. The training of this CAD system is carried of iteratively and collaboratively between different clinical sites, and is orchestrated by a server. The generic or global CAD system 1100 is transmitted from a host server 1150 to a number of different clinical sites 1102-1114 where the CAD system 1100 is trained on image datasets located at those sites 1102-1114. When the local training at each site 1102-1114 is finished, each site 1102-1114 sends the locally trained version of the model to the server. The server then combines or aggregates all the local models into a new global model. This new global model is then broadcasted to the sites 1102-1114, restarting all the process. This is conducted for several global iterations, until convergence is achieved. After the global training, additional personalization steps may be performed at each site, to improve performance. The training of the CAD system 1100 at the particular site 1102-1114 prevents unnecessary transmission and/or exposure of the images outside of the sites 1102-1114, such that privacy of the information contained within the datasets is maintained within the sites 1102-1114, thus providing many advantages in terms of data privacy and data governance. The collaborative training between different sites 1102-1114 allows to leverage data from different sites, and virtually increase the dataset size in which the models are trained.

Based on differences between the types of information or features contained in the training databases at the different sites 1102-1114, i.e., the features extracted from the training dataset at the site 1102-1114 during the training of the CAD system 1100, the CAD system 1100 at each site 1102-1114 is trained with a focus on those features, which can include but are not limited to, types of anomalies, tissues types and characteristics, and patient demographics, e.g., sex, age, race, etc., among other features. Because of data heterogeneity between sites (lesion and pathology drifts, breast density, breast volume, image acquisition systems, postprocessing preferences, other radiological preferences etc.), the CAD system 1100 trained at a specific site 1102-1114 is determined to constitute a model 1116-1124 of the CAD system 100 for analysis of those specific types of features.

Upon completion of the training at the site 1102-1114, the trained CAD systems 1100 are each transmitted back to the server 1150 with only the information from the dataset identifying the features extracted from/identified by the CAD system 100 during the training. The trained CAD systems 100 are models 1116-1124 for use on an imaging system for identifying the features on which the model 1116-1124 was trained, as illustrated by the features identified during the training of the particular model 1116-1124 and retained within the server 1150. Further, if one or more sites 1104-1108 are determined to have sufficient similarity between the features extracted from the training dataset at each site 1104-1108 during training of the CAD system 1100 at those site 1104-1108, the trained system 1100 from each of those sites 1104-1108 can be combined to form a single model 1118, i.e., dynamic clustering of the systems 1100 trained at the sites 1104-1108. The results of the training of the global CAD model 1100 at the various singular or combined sites 1102-1114 results in a library 1126 of models 1116-1124, with each model 1116-1124 specialized on a different data distribution.

However, while the use of the clustered federated learning provides a library 1126 of models 1116-1124 each specialized for use with a particular data distribution or catalog of features, the process of the selection of the model 1116-1124 from the library 1126 requires significant time and effort. For example, when an imaging system is being installed or set up for use at a clinical site, the selection of the CAD model 1116-1124 for instantiation on the imaging system requires an evaluation dataset of representative images from the clinical site.

In prior art systems and methods for the evaluation of different CAD models 1116-1124 for use on an imaging system, model selection is performed by comparing the performance of the set of CAD models 1116-1124 with regard to the evaluation dataset. However, the annotation of the evaluation dataset requires significant time and effort, both in the conversion of the image data into images that can be reviewed and annotated by a radiologist, and in the annotation of those images. Medical image annotation has also a high economic cost. Performance-based model selection has the drawbacks not only of requiring the annotations for the evaluation dataset, but also with regard to the lack of information provided on the performance of the models 1116-1124 with regard to the evaluation dataset. More specifically, in prior art systems and methods for model selection, the only output from the selection is the identification of the model with the best performance on the evaluation dataset, without any information on the reasons why the selected model performed better on the evaluation dataset than others, i.e., there is no ability to interpret why the particular model was selected over others, such as if the selected model was trained on similar features as are present in the evaluation dataset, or if training/evaluation data are distributed similarly.

Finally, each radiologist has certain preferences with regard to the form, manner and type of images produced from the CAD model. However, these preferences with respect to the images for the particular radiologist are not considered in the evaluation of the models 1116-1124 on the evaluation dataset. Thus, even when an appropriate model 1116-1124 is selected, the images provided by the model 1116-1124 must still be modified to provide the preferred and/or desired images to the radiologist for review and diagnostic purposes.

Accordingly, a need exists for a system and method that may be utilized to automatically and optimally select a computer algorithm, or path of algorithms, for executing CAD and diagnosis tasks on an imaging system that overcomes these deficiencies of the prior art.

BRIEF DESCRIPTION OF THE DISCLOSURE

The present disclosure provides a system and method for the determination of a data analysis model to be employed on a data analysis system using an evaluation dataset obtained from the data analysis system in order to optimally configure the data analysis system to provide results to a user without compromising the privacy of the evaluation dataset. The data analysis models are trained in a suitable manner, such as via a federated learning system, among others, to each include various training features associated with each data analysis model. The evaluation dataset can be run through each of the data analysis models to extract features from the evaluation dataset for comparison with the training features of each data analysis model to determine the similarity of the training features of the data analysis models to the extracted features. In conjunction with certain user preferences that can be used along with the evaluation dataset for comparison with the data analysis models, the system and method can determine a data analysis model(s) that best conforms to the analysis requirements of the data analysis system in a fast an automatic manner. The results of the comparison, e.g., the training features of the selected data analysis model(s) and the extracted features, can additionally be presented for review and validation of the selected data analysis model(s). Further, the extraction of the features from the evaluation dataset can be performed on raw data from the data analysis system, or a combination of raw data and annotated data.

According to another exemplary aspect of the disclosure, the data analysis system can be a medical imaging system, with the evaluation dataset including medical image data, and the data analysis models being computer algorithms, machine learning models, or other artificial intelligence models employed for the analysis of medical image data, including but not limited to computer aided detection and diagnosis (CAD) models.

According to one exemplary non-limiting aspect of the disclosure, a medical imaging system includes a radiation source, a detector disposed spaced from the radiation source, a processing device operably connected to the detector for receiving image data from the detector in response to the operation of the radiation source and processing the image data to form images, an electronic storage device operably connected to the processing device on which instruction for the operation of the processing device can be stored, and a medical image data analysis model selection system operably connected to the processing device for performing an automatic selection of a medical image data analysis model for instantiation on the processor, the medical image data analysis model selection system having a server including an electronic storage device including a number of medical image data analysis models stored thereon, and a processor configured to compare extracted features from an evaluation dataset of medical images from the processing device with training features of each of the number of data analysis models, and to provide one or more matched data analysis models for instantiation on the data analysis system.

According to another exemplary non-limiting aspect of the disclosure, an automated model selection system for performing an automatic selection of a data analysis model for instantiation on a data analysis system includes a server including an electronic storage device including a number of data analysis models stored thereon, a processor configured to compare extracted features from an evaluation dataset with training features of each of the number of data analysis models, and to provide one or more matched data analysis models for instantiation on the data analysis system, and a trusted execution environment (TEE) in which to perform the comparison of the training features and the extracted features.

According to still another aspect of one exemplary non-limiting embodiment of the disclosure, a method for selecting a data analysis model for instantiation on a data analysis system includes the steps of providing a server on which is stored a library containing a number of data analysis models therein, providing an evaluation dataset from the data analysis system, processing the evaluation dataset through each of the number of data analysis models to produce extracted features from the evaluation dataset, and comparing the extracted features from the evaluation dataset with training features of each of the number of data analysis models.

It should be understood that the brief description above is provided to introduce in simplified form a selection of concepts that are further described in the detailed description.

BRIEF DESCRIPTION OF THE DRAWINGS

The drawings illustrate the best mode presently contemplated of carrying out the disclosure. In the drawings.

DETAILED DESCRIPTION

Figure 1:
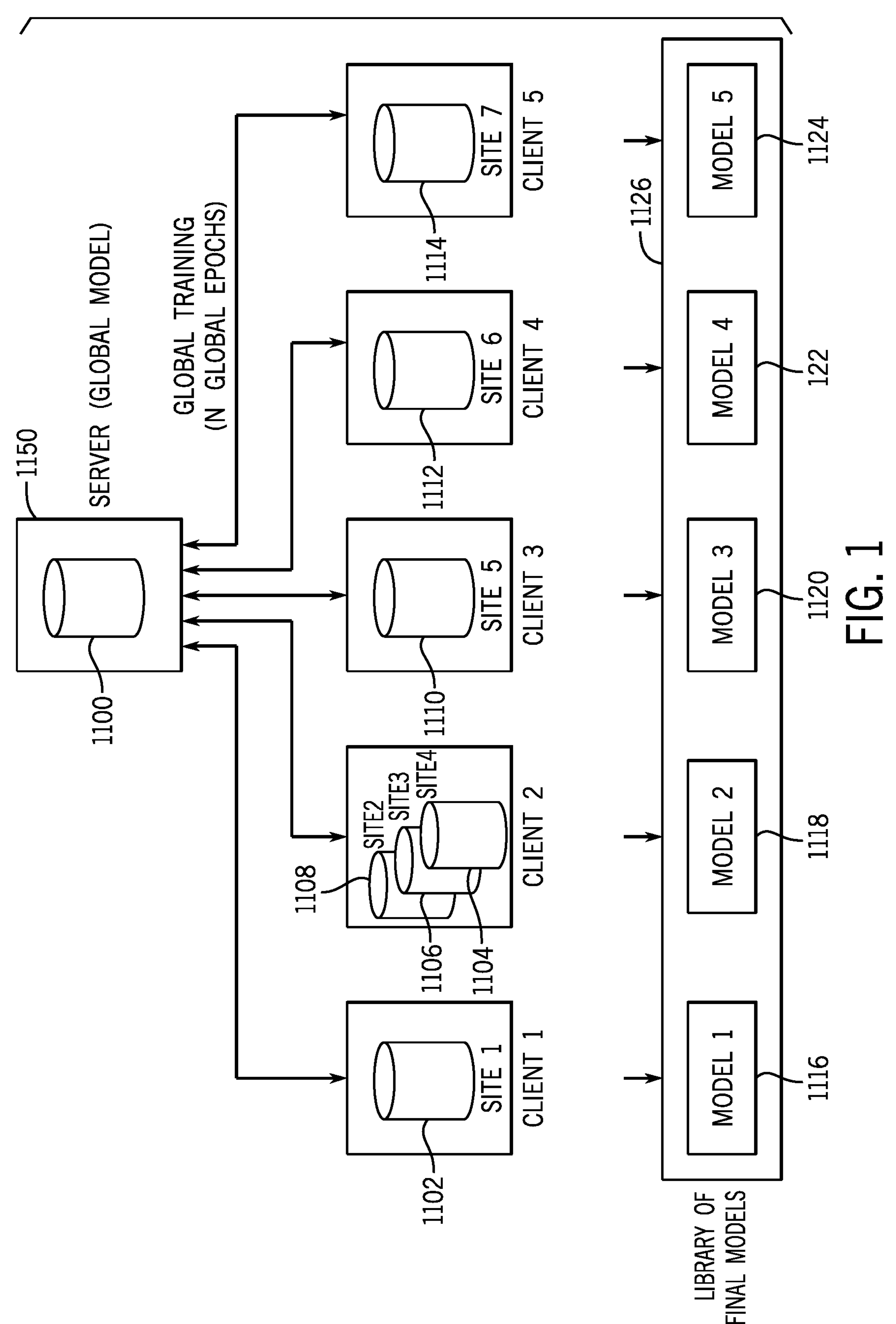
FIG. 1 is a schematic view of a clustered federated learning system for training computer aided detection and diagnosis (CAD) systems for implementation as CAD models to be instantiated on a radiography imaging system.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Medical imaging systems that can be utilized with the system and method of the current disclosure include, but are not limited to, systems performing processes employing various imaging modalities, such as x-ray or radiography systems, computerized tomography (CT) systems, digital breast tomography (DBT) systems, ultrasound (US) systems, electron beam tomography (EBT) systems, magnetic resonance (MR) systems, and combinations thereof. However, virtually any medical device that acquires information from the patient can be employed with the system and method of the current disclosure, where the acquired information is later used to train the model, such as medical devices or systems including, but not limited to electroencephalogram (EEG) devices, electrocardiogram (ECG) devices, connected watches, pacemakers, probes, and insulin injectors.

With particular reference to certain types of radiography imaging systems, the radiography may include a C-shaped arm that carries a radiation source and a radiation detector. The C-shape of the arm allows a physician to access to a patient while the patient is being imaged. In order to obtain medical images of an internal structure at various angles, the C-shaped arm may be rotated to various positions. The following description relates to various embodiments for a medical imaging system with a C-arm. A medical imaging system, such as the medical imaging system shown in FIG. 2, includes a C-arm configured to rotate around at least one rotational axis. The C-arm includes a radiation source and a radiation detector at opposite ends of the C-arm.

Referring to the figures generally, the present disclosure describes systems and methods for a medical imaging system with a C-arm. The medical imaging system described herein (i.e., the medical imaging system depicted in FIG. 2) may be generally referred to as a radiographic medical imaging system, and in particular a mobile C-arm imaging system.

Figure 2:
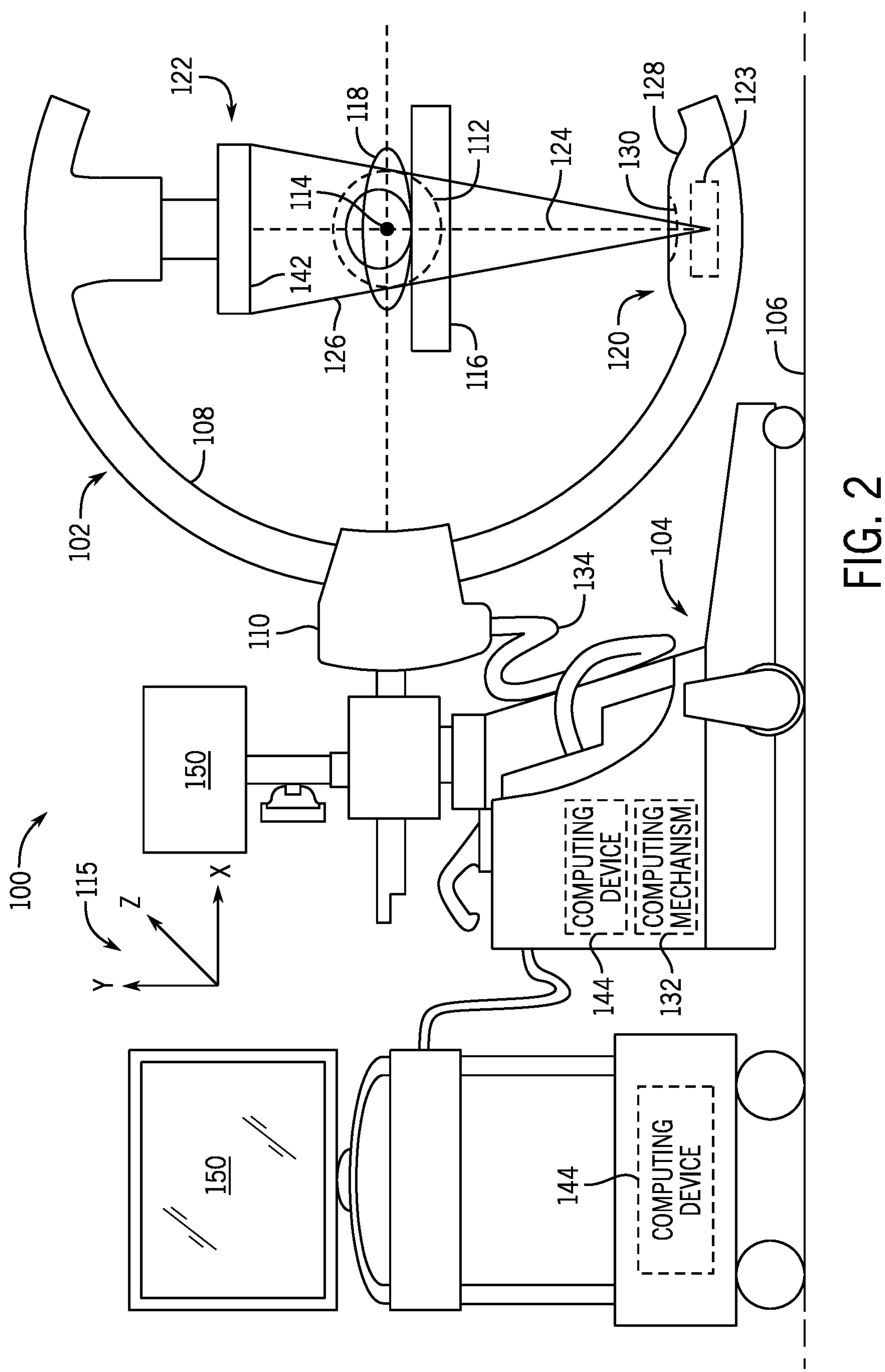
FIG. 2 is a side elevation view of a C-arm imaging device according to one exemplary non-limiting embodiment of the disclosure.

Referring now to FIG. 2, a radiography imaging system 100, which is one example of a data analysis system, such as that disclosed in US Published Patent Application Serial No. US2022/0401048, entitled Imaging System With Carbon Fiber C-Arm, the entirety of which is expressly incorporated herein by reference for all purposes, is shown in accordance with an exemplary embodiment. The radiography imaging system 100 includes a rotatable C-arm 102 that is connected to a base 104. The base 104 supports the C-arm 102 while the C-arm 102 is stationary and while rotating. The base 104 supports the C-arm 102 on a ground surface 106 on which the radiography imaging system 100 sits via a number of wheels 105 or similar rotatable supports that enable the base 104 to be readily moved over and/or along the surface 106 by an operator, such as by grasping handles 107 on the base 104 and pulling or pushing the radiography imaging system 100 into the desired position for the operation of the radiography imaging system 100. The C-arm 102 includes a C-shaped portion 108 that is connected to an extended portion 110. The extended portion 110 is rotatably coupled to the base 104 which allows the C-arm 102 to rotate about an examination region 112 and a rotational axis 114. For example, the C-arm 102 may be configured to rotate at least 180° in opposing directions relative to the base 104, though in some embodiments, the C-arm 102 may be configured to rotate at least 220°. Configuring the C-arm 102 to rotate at least 220° may provide a physician with greater access to a patient being imaged. While the following describes the rotation of the C-arm 102 as rotating in the X and Y directions of the Cartesian coordinate system 115 (i.e., rotating the C-shaped portion 108 such that opposing ends of the C-shaped portion 108 are closer to or further from the extended portion 110 in various positions), it is understood that the C-arm 102 may also rotate in the Z direction (i.e., rotating the C-shaped portion 108 such that opposing ends of the C-shaped portion 108 are closer to or further from a head of the patient within the examination region 112 in various position and/or changing the elevation of the extended portion 110 relative to the base 104 employing a suitable vertical translation mechanism (not shown) disposed on the base 104 and engaged with the extended portion 110.

The radiography imaging system 100 further includes a patient support 116 (i.e., couch, bed, table, etc.) that supports an object or patient, such as a patient 118 while at least a portion of the patient 118 is within the examination region 112. The medical imaging system 100 additionally includes a radiation source 120 and a radiation detector 122. The radiation source 120 and the radiation detector 122 are supported by and rotate with the C-arm 102. Furthermore, the radiation source 120 and the radiation detector 122 are positioned at opposite ends of the C-shaped portion 108 of the C-arm 102 along axis 124, where axis 124 intersects and extends radially relative to the rotational axis 114. The C-shaped portion 108 may be rotated as described above in order to adjust the position of the radiation source 120) and the radiation detector 122 to obtain 2D projection images of the subject 118 at each selected orientation of the radiation source 120 relative to the detector 122 in order to form a 2D projection dataset. Furthermore, in the embodiment depicted in FIG. 2, the position of the radiation detector 122 may be varied such that the radiation detector 122 is placed further from or closer to the radiation source 120.

During a medical imaging procedure, a portion of the patient 118 is within the examination region 112 and the radiation source 120 emits radiation 126. In one embodiment, the radiation source 120 may include an X-ray tube 123 housed within a casing 128. The X-ray tube generates the radiation 126 which escapes the casing 128 via an outlet 130. The radiation 126 traverses the examination region 112 and is attenuated by the portion of the patient 118 that is within the examination region 112. Specifically, the radiation source 120 emits the radiation 126 towards the radiation detector 122 which is on the opposite end of the C-arm 102. The radiation source 120 emits cone-shaped radiation which is collimated to lie within an X-Y-Z plane of the Cartesian coordinate system 115 which is generally referred to as an "object plane" which is parallel to the radiation detector 122 at an isocenter of the C-arm 102.

After passing through a portion of the patient 118, the attenuated radiation is captured by the radiation detector 122. In some embodiments, the radiation detector 122 includes a plurality of detector elements (not shown) that acquire projection data. Each detector element produces an electrical signal that is a measurement of the attenuation at the detector element location. The attenuation measurements from all the detector elements in the detector 122 are acquired separately to produce a transmission profile. In one embodiment, the radiation detector 122 is fabricated in a flat panel configuration including a plurality of detector elements.

When the radiation source 120 and the radiation detector 122 are rotated with the C-arm 102 within the object plane and around the patient 118, the angle at which the radiation 126 intersects the patient 118 changes. A group of attenuation measurements (i.e., projection data) form the radiation detector 122 at one C-arm angle is referred to a "view." A "scan" of the patient 118 includes a set of projection views made at different angles, or view angles, during rotation of the C-arm 102. As used herein, the term view is not limited to the use described herein with respect to projection data obtained from or from one C-arm 102 angle. The term view is used to mean one data acquisition whenever there are multiple acquisitions from different angles, such as used to form the 2D projection dataset.

The radiography imaging system 100 further includes a control mechanism 132 that is housed within the base 104. The control mechanism 132 is connected to the C-arm 102, the radiation source 120, and the radiation detector 122 via a cable 134 which allows the control mechanism to send data to/receive data from the C-arm 102, the radiation source 120, and the radiation detector 122. The control mechanism 132 controls the rotation of the C-arm 102 and the operation of the radiation source 120. While FIG. 1 depicts the base 104 as including the control mechanism 132, in other embodiments the control mechanism may be separate from the base 104 (i.e., in a different room).

The C-arm 102 may be adjusted to a plurality of different positions by rotation of the C-shaped portion 108. For example, the radiation detector 122 may be positioned vertically above the radiation source 120 relative to the surface 106 on which the medical imaging system 100 sits, with axis 124 arranged normal to the surface 106 intersecting a midpoint of the outlet 130 of the radiation source 120 and a midpoint of a detector surface 142 of the radiation detector 122. The C-arm motor controller 138 and a guide system within the extended portion 110 may adjust the C-shaped portion 108 from the first position to a different second position by rotating the C-shaped portion 108 via a coupling between the guide system and the C-shaped portion 108. In one example, the second position may be a position in which the radiation source 120 and the detector 122 are rotated 180° together relative to the first position such that the radiation source 120 is positioned vertically above the radiation detector 122, with the axis 124 intersecting the midpoint of the outlet 130 of the radiation source 120 and the midpoint of the detector surface 142 of the radiation detector 122. When adjusted to the second position, the radiation source 120 may be positioned vertically above the rotational axis 114 of the C-shaped portion 108 and the radiation detector 122 may be posited vertically below the rotational axis 114.

The medical imaging device or system 100 further includes a computing device 144 that is housed within the base 104 that is operable to generate images for presentation on a display 150. While FIG. 2 depicts the computing device 144 as housed within the base 104, in other embodiments the computing device 144 may be remote from the rest of the radiography imaging system 100. As used herein, a computing device (or system) is any device/system capable of processing, storing, and/or transmitting data (i.e., tablet, handheld device, smartphone, personal computer, laptop, network computer, server, mobile communication device, etc.). The computing device 144 may be connected to a network (i.e., a wide area network (WAN), a local area network (LAN), a public network (the internet), etc.) which allows the computing device 144 to communicate with other devices on a same network. In some embodiments, the network may be regarded as a private network and may include, for example, a virtual private network.

Figure 3:
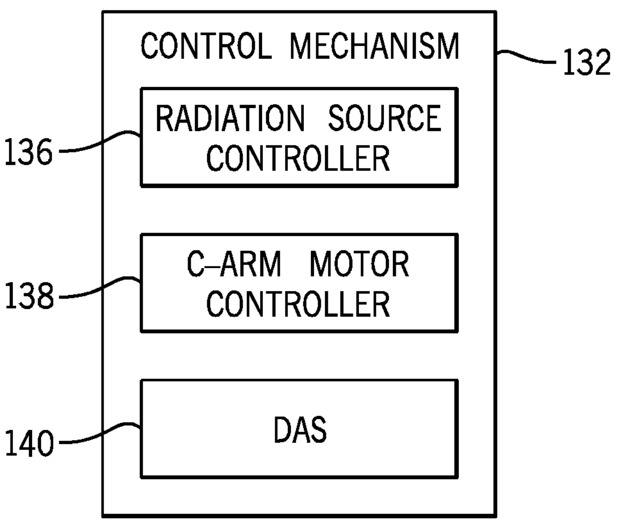
FIG. 3 is a block diagram of a control mechanism for the radiography medical imaging device of FIG. 2 according to one exemplary non-limiting embodiment of the disclosure.

Briefly turning to FIG. 3, a block diagram of the computing device 144 is shown in accordance with an exemplary embodiment. The computing device 144 includes a processing device 146 and a system memory 148. In some embodiments, the computing device is connected to a display 150 and one or more user input devices, e.g., a touchscreen, a keyboard, a mouse, etc., and/or external devices 152. The processing device 146 is in communication with the system memory 148 and may execute computer readable program instructions stored in the system memory 148. As used herein, a processor may include a central processing unit (CPU), or other electronic components capable or executing computer readable program instructions (i.e., a digital signal processor, a field-programmable gate array (FPGA), a graphics processing unit (GPU), etc.). Furthermore, as used herein, a processor may include two or more of a CPU, a digital signal processor, an FPGA, and a GPU.

The system memory 148 is a computer readable storage medium. As used herein, a computer readable storage medium is any device that stores computer readable program instructions for execution by a processor and is not construed as transitory per se. Computer readable program instructions include programs, logic, data structures, modules, etc. that when executed by a processor create a means for implementing functions/acts. Computer readable program instructions when stored in a computer readable storage medium and executed by a processor direct a computer system and/or another device to function in a particular manner such that a computer readable storage medium comprises an article of manufacture. System memory as used herein includes volatile memory (i.e., random access memory (RAM) and dynamic RAM (DRAM)) and nonvolatile memory (i.e., flash memory, read-only memory (ROM), magnetic computer storage devices, etc.). In some embodiments the system memory 148 may further include cache.

In one embodiment, the various methods and processes may be stored as computer readable program instructions in the system memory 148. In this embodiment, the system memory 148 includes computer readable program instructions for imaging a patient with a medical imaging system (i.e., the radiography imaging system 100).

The external devices 152 include devices that allow a user to interact with/operate the computing device 144 (i.e., mouse, keyboard, touchscreen, speakers, etc.), and can include the display 150 when configured as a touchscreen device. In some embodiments, the display 150 displays a graphical user interface (GUI). The GUI includes editable fields for inputting data (i.e., patient data, imaging parameters, etc.) and further includes selectable icons. Selecting an icon and/or inputting data causes the processing device 146 to execute computer readable program instructions stored in the system memory 148 which causes the processor to perform a task. For example, a user of the computing device 144 may use an external device 152 or the touchscreen display 150 to select a "start" icon or the like which causes the processing device 146 to being a medical imaging procedure and/or analysis according to one or more embodiments as disclosed herein.

Radiography imaging system 100 may include one computing device 144. The computing device 144 may be used for inputting or outputting imaging parameters, requesting examinations, plotting data, and/or viewing images. Furthermore, in certain embodiments, the radiography imaging system 100 may be coupled to multiple displays, printers, workstations, and/or similar devices located either locally or remotely (i.e., within an institution or hospital or in a an entirely different location, etc.) via one or more configurable wired and/or wireless networks. Furthermore, in some embodiments, the base further house an internal power source (not shown) that provides electrical power to operate the radiography imaging system 100. Alternatively, the base 104 may be connected to an external power source to power the radiography imaging system 100. A plurality of connection cables may (i.e., cable 134) may be provided to transmit electrical power to the radiation source 120, the radiation detector 122, etc.

The computing device 144 is in communication with and provides commands to the radiation source controller 136, the C-arm motor controller 138, and the DAS 140 for controlling system operations such as data acquisition and/or data processing. In some embodiments, the computing device 144 controls operation of the radiation source controller 136, the C-arm motor controller 138, and the DAS 140 based on a user input.

Computing device 144 also includes a data analysis model 159, such as a computer aided detection and diagnosis (CAD) system 160, that is configured to receive an image dataset, such as a 2D projection image dataset/transmission dataset (not shown), from the detector 120 and to implement various anomaly detection methods described herein. The CAD system 160 may be implemented as a piece of hardware that is installed in the processing device 146. Optionally, the CAD system 160 may be implemented as a set of instructions that are installed on the processing device 146. The set of instructions may be stand-alone programs, may be incorporated as subroutines in an operating system installed on the processing device 146, and/or in system memory 148 to be accessed by the processing device 146, may be functions that are installed in a software package on the processing device 146, or may be a combination of software and hardware. It should be understood that the various embodiments are not limited to the arrangements and instrumentality shown in the drawings.

Figure 4:
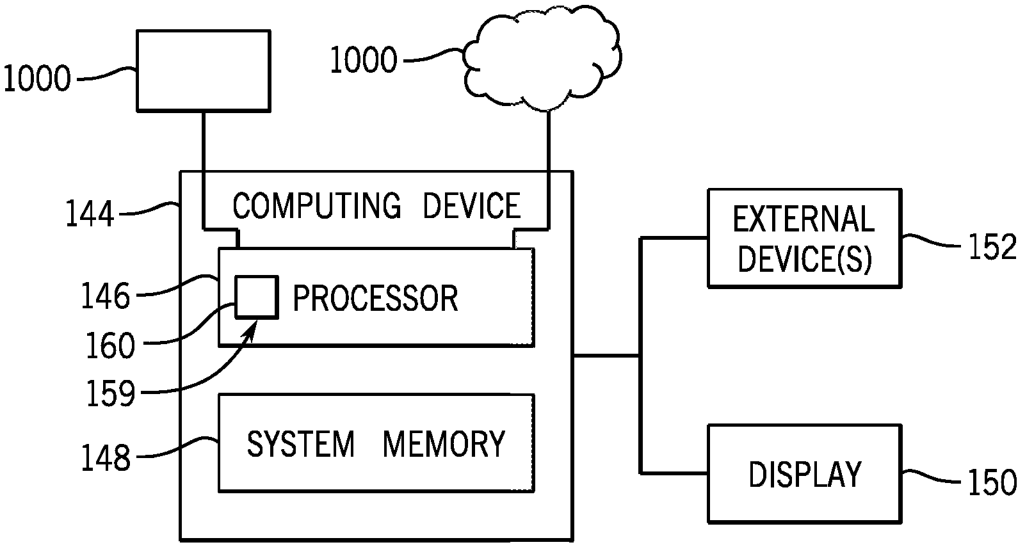
FIG. 4 is a block diagram of a computing device for the radiography medical imaging device of FIG. 2 according to one exemplary non-limiting embodiment of the disclosure.
Figure 5:
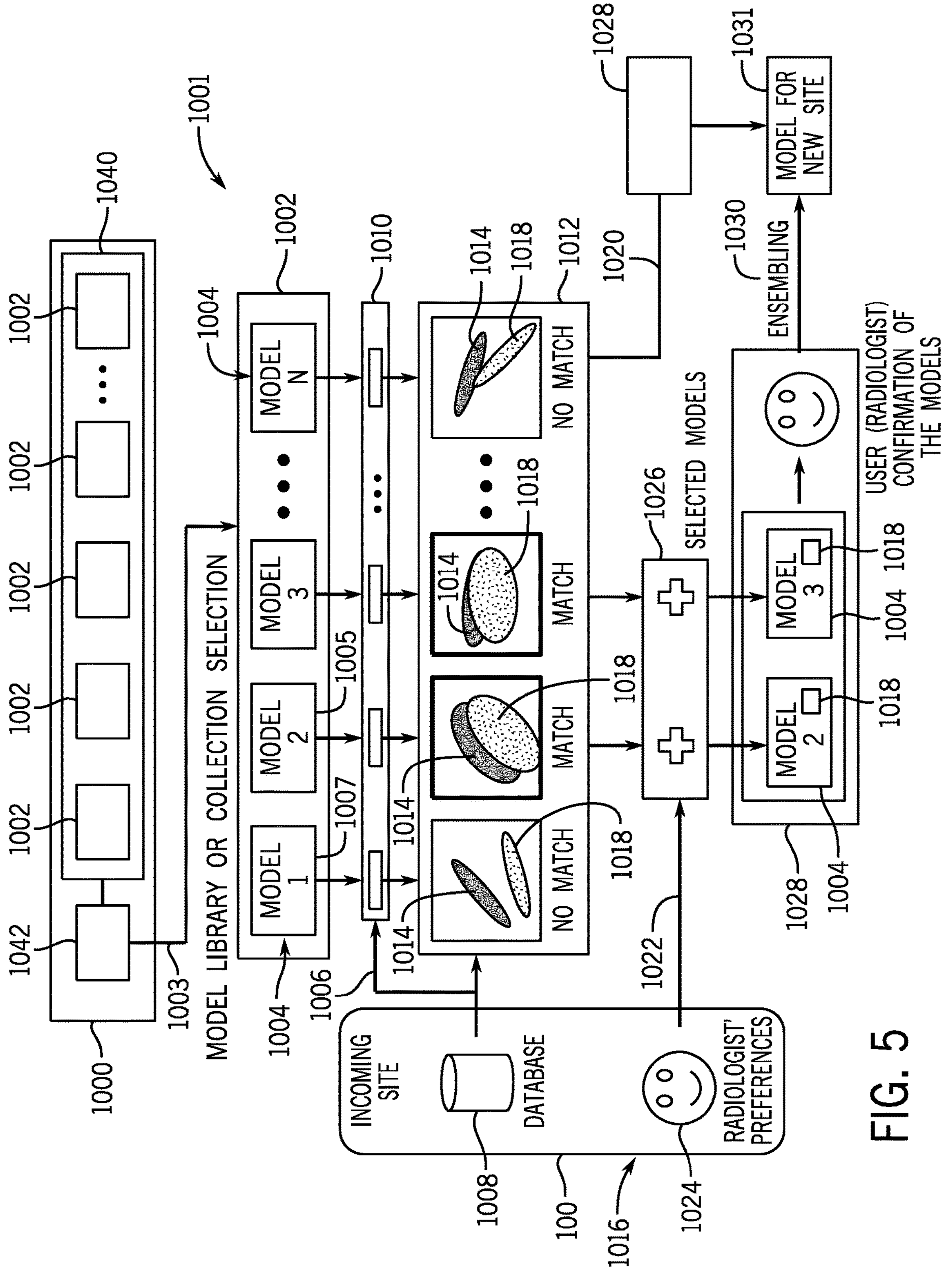
FIG. 5 is a schematic view of a first embodiment of an automatic model selection system and process according to one exemplary non-limiting embodiment of the disclosure.

Looking now at FIGS. 4 and 5, a flowchart of an automated model selection system 1000 and associated method 1001 employed for the selection of the CAD system 160 for implementation on the radiography imaging system 100 and is illustrated in accordance with various embodiments. The system 1000 and method 1001 may be implemented as a set of instructions on a central or cloud server 1000 including a computing device or processor 1042 separate from the processing device 146 as shown in FIG. 4. More specifically, the system 1000 and method 1001 may be provided as a non-transitory machine-readable medium or media having instructions recorded in an electronic storage device 1040 therein or an algorithm or artificial intelligence stored thereon for selecting the form of the CAD system 160 to be instantiated on the imaging system 100 in association with the processing device 146. The medium or media may be any type of CD-ROM, DVD, floppy disk, hard disk, optical disk, flash RAM drive, or other type of computer-readable medium or a combination thereof.

In the method 1001, in initial step 1003 a library or collection 1002 of data analysis models 1004 is selected from a number of libraries 1002 stored within the system 1000, such as within an electronic storage device 1040. The storage device 1040 is operably connected to the processor 1042 within the server 1000 that is operable, such as by using instructions for the operation of the processor 1042 to perform the steps of the method 1001.

In the illustrated exemplary embodiment of FIG. 5, the data analysis models 1004 are medical image data analysis models or CAD models 1005 in which the CAD models

1005 in each library 1002 correspond to a type of imaging to be performed on and/or the type tissue to be imaged by the particular imaging system 100. However, the libraries 1002 and/or analysis models 1004 can be configured for the analysis of many different types of information from different data analysis systems, i.e., in addition to detection of anomalies within the image data/images, such as at the patient level, by collecting patient information (density, ethnicity, age, patient history, etc.), for use in patient screening, and/or the diagnosis of anomalies detected within the image data, among others. Any number of data analysis models 1004 can be contained within each library 1002, with each of the analysis models 1004 having been trained in a suitable manner for data analysis on a data analysis system, e.g., to detect and identify anomalies and/or tissue types within image data obtained in an imaging procedure performed by an imaging system similar to imaging system 100. In a particular exemplary embodiment for the generation of the CAD models 1005 within the library 1002, the CAD models 1005 can be formed using a clustered federated learning process similar to that illustrated in FIG. 1.

After selection of the appropriate library 1002 and CAD models 1005 related to the imaging system 100, in step 1006 of the method 1001, an evaluation dataset or database 1008 of medical images previously obtained using the radiography imaging system 100 is provided from the clinical site/imaging system 100 to the model selection system 1000. The evaluation dataset 1008 contains image data obtained from a number of imaging procedures performed by the radiography imaging system 100 and provides a representation of the patient distribution of the clinical site where the radiography imaging system 100 is operated. As opposed to annotated images, the evaluation dataset 1008 takes the form of raw image data or images without annotations, thus reducing the time and effort required for the overall method 1001 of determination of the appropriate model 1004/1005.

In step 1010 the evaluation dataset 1008 is applied to each of the models 1004/CAD models 1005 in order to extract the features 1014 from the evaluation dataset 1008 that are utilized in the operations performed by the models 1004/CAD model 1005. The features 1014 can be any form of descriptors, adjectives, aspects or other identifying information regarding the image data in the evaluation dataset 1008, and can be extracted automatically by the models 1004 without the need of explicit human intervention. For example, where the radiography imaging system 100 is a mammography imaging system, the features 1014 can be one or more of mean breast density, lesion location, geographic location, lesion sizes, lesion types, lesion characteristics (e.g., information on the contours, sparsity of microcalcifications, tissue surrounding the lesions, etc.), population ages, genders, races, etc. In one exemplary embodiment, the extraction of the features 1014 from the evaluation dataset 1008 can take the form of a forward pass of the evaluation dataset 1008 through each model 1004/CAD model 1005 to retrieve the features 1014. The features 1014 provide an indication of the characteristics of the images produced at the clinical site 1016 by the radiography imaging system 100, such that a model 1004/CAD model 1005 trained on similar or the most highly related features to the features 1014 can be determined.

In step 1012, the extracted features 1014 are compared to the training features 1018 associated with each of the models 1004/CAD models 1005 and stored within the server 1000 in association with each model 1004/CAD model 1005. The comparison performed by a similarity metric to determine the similarities between the extracted features 1014 and the training features 1018 of each model 1004/CAD model 1005. The training features 1018 are determined for each model 1004/CAD model 1005 during training of the model 1004/CAD model 1005 at a particular site and constitute the features of the data, e.g., image data, at the training site used to train the model 1004/CAD model 1005. The comparison of the extracted features 1014 and the training features 1018 is performed by applying data mining techniques in a high-dimensionality feature space, to measure the degree of similarity between the extracted features 1014 and the training features 1018 and select the model 1004/1005 or group of models 1004/1005 that are the most relevant or best adapted to use with the clinical site/radiography imaging system 100. The degree of similarity can be measured with different techniques, metrics or criterions, depending on the topology and/or characteristics of the feature space, including but not limited to clustering metrics. For instance, the features in the feature space could be (without limiting to) vectors, matrices, or tensors, formed by different numerical values (integers, real numbers, bounded real numbers), categorical values, and/or a combination of all of them. Some of the metrics or criterions for determining the match or similarity results between extracted features and features used during training could be threshold-based. In those cases, the thresholds (which can be given in the form of absolute values or percentages) could be either set during the development of the product, and might be different for each application, or be fixed from the user's preferences (or a combination of both). In the case of data analysis models 1004 that take the form of AI systems that contain a feature extractor, like most Deep Learning-based CAD systems 1005, this analysis can be performed by extracting the features at one or more intermediate layers of the neural networks and applying some of the aforementioned similarity metrics. The AI models 1004 need not to be specifically trained for performing these similarity comparisons. The results of the comparison in step 1012 provide a match/no match indication for each of the models 1004/CAD models 1005 with regard to the evaluation dataset 1008.

After identification of the matching models 1004/CAD models 1005, in step 1020 if there is a single matching or best matched model 1004/CAD model 1005, the system 1000 outputs the matching model 1004/CAD model 1005 for instantiation on the imaging system 100.

Alternatively, if the comparison results in more than one matching model 1004/CAD model 1005, in step 1022 the system 1000 can solicit/receive a set of user preferences 1024 from the clinical site/radiography imaging system 100. The set of user preferences 1024 contains user-selected settings for one or more of the operation of the imaging system 100, the determination of the presence of various structures and/or lesions in images obtained by the imaging system 100 and/or the manner of the display of the images and any structures and/or lesions identified therein by the radiography imaging system 100. These preferences contained in the set of user preferences 1024 can be compared with the training features 1018 of the selected or matched models 1004/CAD models 1005 by the system 1000 in step 1026 to further refine the similarity results and/or identification and selection of matching models 1004/CAD models 1005. For this, a particular encoding or embedding can be applied to the set of user preferences 1024 to map them to the space in which the training features lie, making the comparison possible. The encoding or embedding of the preferences can be done with any of the state-of-the-art methods used to map numerical or categorical variables to a feature space (including but not limited to one-hot encoding, integer encoding, feature hashing, embedding layers, etc.). The encoding methods must be previously calibrated to allow for a correct mapping of the preferences to the learnt feature space, after the model has been completely trained. This calibration can be done by manually analyzing the extracted features, or by using some Machine Learning algorithm or any other data driven technique. If the model is re-trained, the calibration must be reconducted. Another option is to train the model by making sure that the extracted features are mapped to the variables that can or might be contained in the user preferences. This would remove the need for re-calibrating the user preferences encoding if the model is to be re-trained. The comparison in step 1026 can be performed in any suitable manner, such as by employing a suitable similarity metric applicable to user preferences in manner similar to the comparison of the extracted features 1014 with the training features 1018 in step 1012. User preferences 1024 can also modify the metrics and/or criterions used for calculating the similarity results between features 1014,1018 and can therefore be incorporated before the calculation of the similarity results.

If the comparison of the set of user preferences 1024 with the selected or matched models 1004/CAD models 1005 results in a single final selected or matched model 1004/CAD model 1005, then the final matched model 1005 is displayed to the user/radiologist along with the trained features 1018, as well as optionally the extracted features 1014, the similarity results and combinations thereof, for the final matched model 1004/CAD model 1005. By displaying the trained features 1018, in step 1028 the user/radiologist can validate the final matched model 1004/CAD model 1005 as being appropriate for the imaging system 100 prior to instantiation of the final matched model 1004/CAD model 1005 on the imaging system 100. The degree of matching between the training features 1018 and evaluation/extracted features 1014 can be displayed to the user/radiologist, by displaying different types of visualizations of the features 1014,1018, or statistics between the training features 1018 and evaluation/extracted features 1014 that illustrate similarity, or the values of the similarity metrics and/or criterions used for the matching, the extracted features, the similarity results, and combinations thereof, or some appropriate graphical representation of them. An auxiliary AI algorithm (not shown) could also be used for translating the feature similarity results to natural language, which is easily understood by humans. The similarity result in its natural language version can then be outputted in any way that is found convenient and that improves the user experience, including but not limited to in the form of text in a screen or by speakers. In a more general way, the user-system interaction could be managed in any way found convenient for communication of the results to the user, including but not limited to, prompt commands, text, touch screen, voice, etc.

However, in the event that more than one final matched model 1004/CAD 1005 is selected after the comparison of step 1026, after validation of each of the final matched models 1004/CAD models 1005 in step 1028, in step 1030 the system 1000 can ensemble or combine the final matched models 1004/CAD models 1005 into a single matched model 1004/CAD model 1005 for instantiation on the imaging system 100. The method for ensembling or combining the model can be any of the current state-of-the-art methods, or any other method that allows to combine one or more models, and can also benefit from the set of user preferences 1024 for finding a more appropriate model combination.

Figure 6:
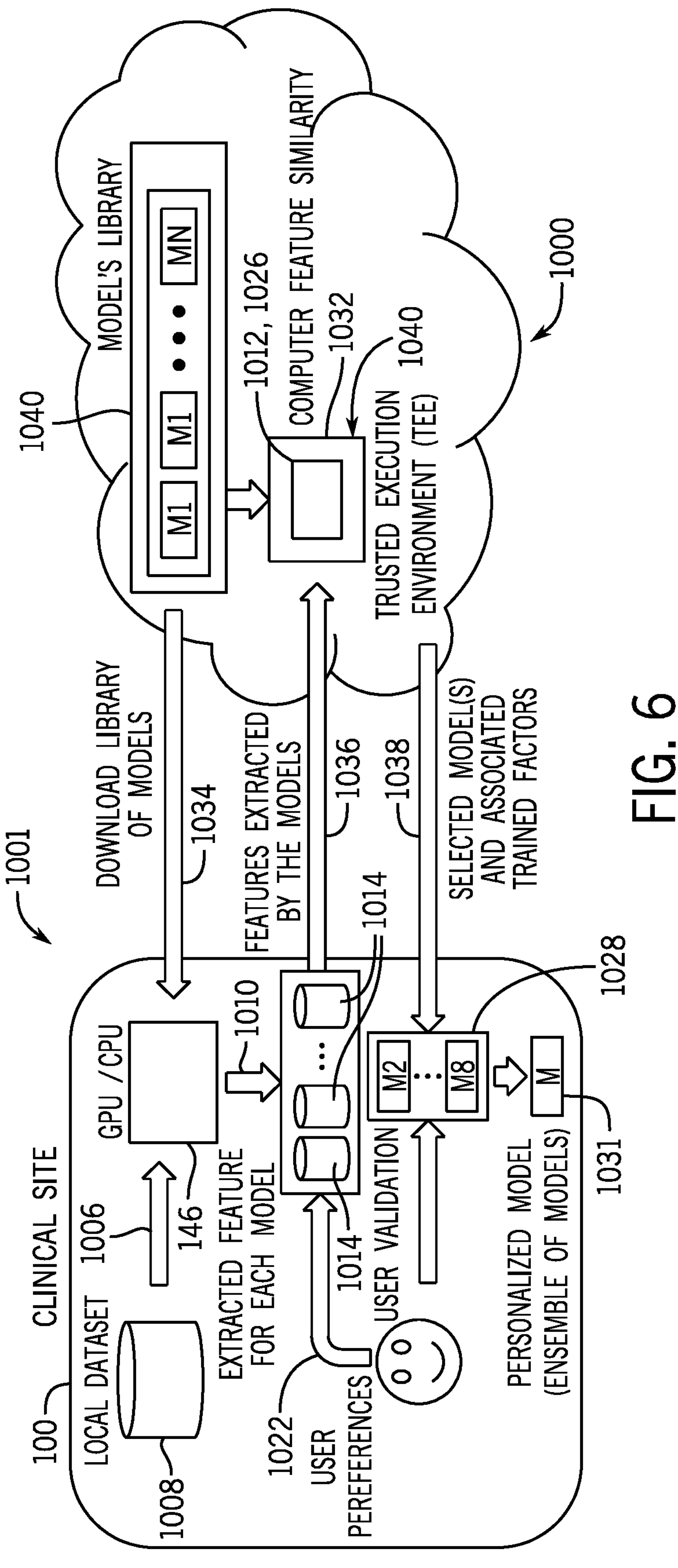
FIG. 6 is a schematic view of a second embodiment of an automatic model selection system and process according to one exemplary non-limiting embodiment of the disclosure.

In an alternative embodiment for the model evaluation and selection system 1000 and associated method, with regard to FIG. 6 the library 1002 of the models 1004/CAD models 1005 can be downloaded or otherwise transmitted to the clinical site/imaging device 100 in step 1034 to be accessed by the processing device 146. Thus, the evaluation dataset 1008 remains within the clinical site/imaging system 100 when run through the various models 1004/CAD models 1005 within the downloaded library 1002 in order to produce the extracted features 1014 from the evaluation dataset 1008. Subsequently, it is only the extracted features 1014 that are transmitted from the clinical site/imaging system 100 to the server/evaluation system 1000 in step 1036 for comparison with the trained features 1018 in step 1012, which can be performed within the server/cloud/evaluation system 1000 on a trusted execution environment (TEE) 1032 on the processor 1040 using homomorphic encryption, or any other Differential Privacy techniques for increasing data privacy, and contained on the evaluation system 1000.

In another alternative embodiment, the library 1002 of models 1004/CAD models 1005 and their associated training features 1018 can be downloaded to the clinical sites 100. The comparison between the evaluation/extracted features 1014 and the training features 1018 can then be performed at the clinical site 100, such that not even the extracted features 1014 leave the clinical site 100. Again, all the similarity calculations, as well as any other operation that involves the training features 1018 and the evaluation/extracted features 1014 are carried on trusted execution environments (TEE) 1032 and using homomorphic encryption and/or differential privacy techniques. The choice between these two embodiments shall depend on the collaboration contracts of all the clinical sites used for training the models 1004/.CAD models 1005 in the library 1002.

Additionally, the user preferences 1024 can be combined with the extracted features 1014 for transmission to the server/evaluation system 1000, such that the comparison of the extracted features 1014 and the user preferences 1024 with the trained features 1018 can take place simultaneously to determine the one or more matched models 1004/CAD models 1005 from the library 1002. The one or more matched models 1004/CAD models 1005 determined by the evaluation can then be provided to the user in step 1038 along with the trained features 1018 for each model 1004/CAD model 1005 to enable the user to validate one or more of the models 1004/CAD models 1005, as discussed previously. Once the one more models 1004/CAD models 1005 have been validated by the user in step, the validated and personalized model 1004/CAD model 1005 can be instantiated at the clinical site/imaging system 100, optionally with an ensembling of more than one model 1004/CAD model 1005 is more than one model 1004/CAD model 1005 is validated by the user. The non-selected and/or non-validated models 1004/CAD models 1005 can then be deleted from the clinical site/radiography imaging system 100.

In still another alternative exemplary embodiment, if the evaluation dataset 1008 includes image(s)/image data having annotations thereon, the annotations can be used to create a performance metric for combination with similarity metric for comparison purposes. The performance metric can be evaluated with regard to the comparable attributes for the various models 1004/CAD models 1005, including but not limited to one or more of appropriate use criteria (AUC), sensitivity, specificity, false positive rate (FPR), and combinations thereof. The results of this comparison can be utilized in conjunction with the results of the comparison of the extracted features 1014 with the trained features 1018 to determine the selected model(s) 1004/CAD model(s) 1005, either prior to or in association with the use of the user preferences 1024.

Figure 7:
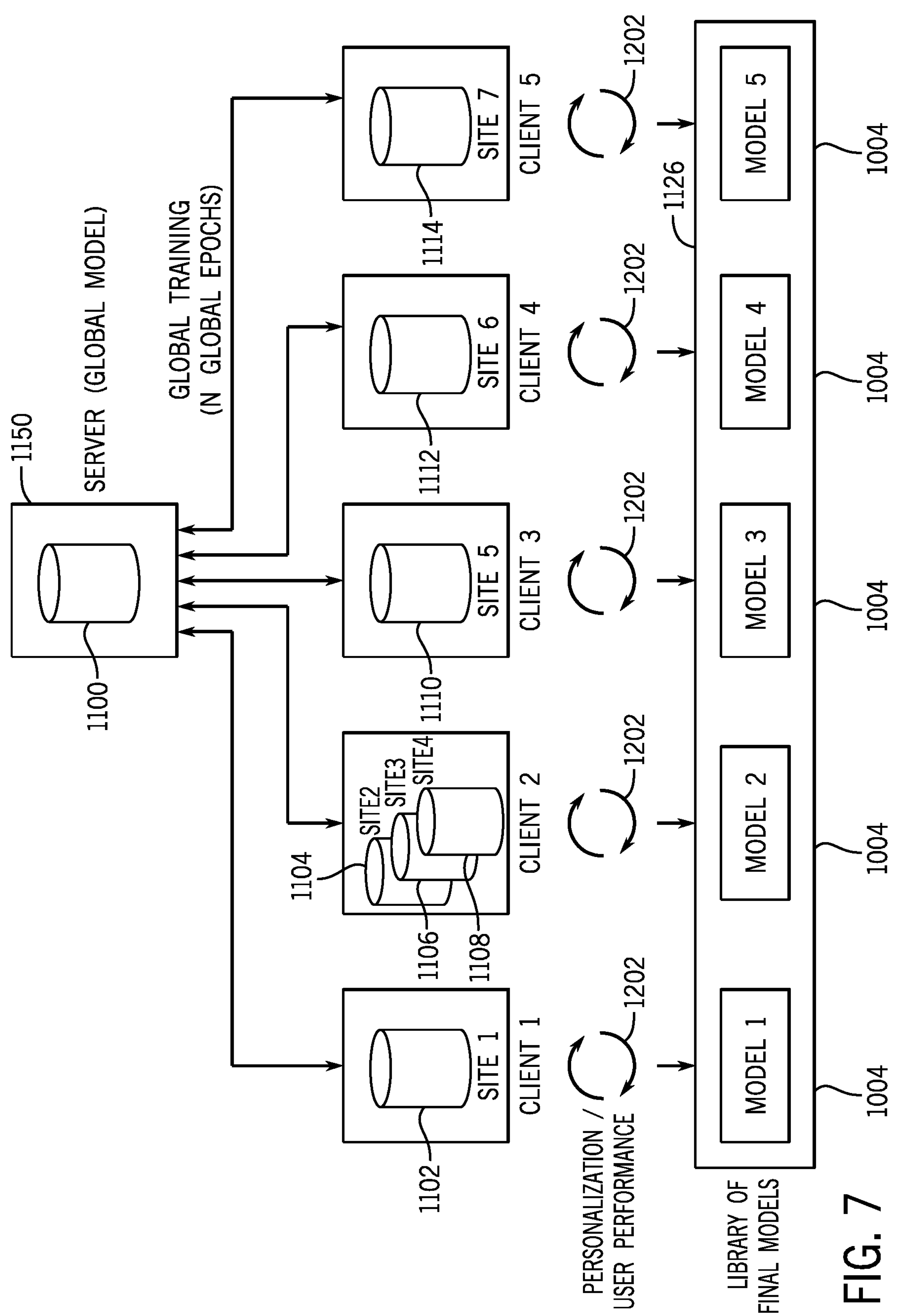
FIG. 7 is a schematic view of a clustered federated learning system for training computer aided detection and diagnosis (CAD) systems for implementation as CAD models including sample user preferences as training features.

Also, with reference now to FIG. 7, in another exemplary embodiment of the disclosure, the training method 1200 of the artificial intelligence (AI), machine learning (ML) or other computer algorithm data analysis models 1004/CAD models 1005, such as in the clustered federated learning process, can be modified to include user preferences 1202 into the training features 1018 for comparison with the actual user preferences 1024 provided during the selection process/method 1001 performed by the system 1000.

In addition to each of the above embodiments, the radiography imaging system 100 can be any type of data analysis system 100 requiring a data analysis model 1004 thereon. Other examples of data analysis systems can be PCs, workstations, cloud services, IoT devices, or any other imaging system like x-ray or radiography systems, computerized tomography (CT) systems, digital breast tomography (DBT) systems, ultrasound (US) systems, electron beam tomography (EBT) systems, magnetic resonance (MR) systems, and combinations thereof. The data analysis model 1004 for instantiation on the data analysis system 100 can be selected from a library 1002 of models 1004 according to any of the prior described and/or illustrated embodiments.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for selecting a data analysis model for instantiation on a data analysis system, the method comprising:

a. providing a server on which is stored a library containing a number of data analysis models therein;
b. providing an evaluation dataset from the data analysis system;
c. processing the evaluation dataset through each of the number of data analysis models to produce extracted features from the evaluation dataset; and
d. comparing the extracted features from the evaluation dataset with training features of each of the number of data analysis models, wherein the step of providing the library containing the number of data analysis models comprises:

i. providing a global data analysis model for analysis of data from a data analysis system;
ii. downloading copies of the global data analysis model to a number of sites; and
iii. training of the copies of the global data analysis model using training data at each site to form the number of data analysis models.

2. The method of claim 1, wherein the training of the copies of the global data analysis model comprises incorporating user preferences within the training data.

3. The method of claim 1, wherein the step of comparing the extracted features from the evaluation dataset to the training features comprises applying a similarity metric to the extracted features and the training features to determine similarity results.

4. The method of claim 3, further comprising the steps of:

a. identifying one or more of the number of data analysis models having training features matching the extracted features after comparing the extracted features with the training features with the similarity metric to form a set of one or more matched data analysis models; and
b. presenting the set of one or more matched data analysis models.

5. The method of claim 4, further comprising the step of displaying the training features, the extracted features, the similarity results, and combinations thereof for each of the one or more matched data analysis models in conjunction with the set of one or more matched data analysis models for validating the set of one or more matched data analysis models.

6. The method of claim 5, further comprising the step of ensembling the set of one or more matched data analysis models when more than one matched data analysis model is validated.

7. The method of claim 1, further comprising the step of downloading the number of data analysis models onto the data analysis system prior to processing the evaluation dataset through each of the number of data analysis models to produce extracted features from the evaluation dataset.

8. The method of claim 7, further comprising the step of transmitting the extracted features from the data analysis system to the server prior to comparing the extracted features from the evaluation dataset with training features of each of the number of data analysis models.

9. The method of claim 7, wherein the step of downloading the number of data analysis models onto the data analysis system further comprises downloading the training features for each model from the library onto the data analysis system.

10. The method of claim 1, wherein the data analysis system is a medical imaging system.

11. The method of claim 9, wherein the number of data analysis models are a number of computer aided detection and diagnosis models.

12. The method of claim 1, wherein the evaluation dataset comprises medical image data without annotations.

13. An automated model selection system for performing an automatic selection of a data analysis model for instantiation on a data analysis system, the model selection system comprising:

a. a server including an electronic storage device including a number of data analysis models stored thereon;
b. a processor configured to compare extracted features from an evaluation dataset with training features of each of the number of data analysis models, and to provide one or more matched data analysis models for instantiation on the data analysis system; and
c. a trusted execution environment (TEE) in which to perform the comparison of the training features and the extracted features, wherein the number of data analysis models are formed by training copies of a global data analysis model at a number of sites using training data at each site to form the number of data analysis models.

14. The model selection system of claim 13, wherein processor is configured to compare a similarity of the extracted features with the training features of each of the data analysis models.

15. The model selection system of claim 13, wherein the evaluation dataset is a medical image dataset that does not contain annotations.

16. The model selection system of claim 13, wherein the processor is configured to provide the training features for the one or more matched data analysis models along with the one or more matched data analysis models.

17. A medical imaging system comprising:

a. a radiation source;

b. a detector disposed spaced from the radiation source;

c. a processing device operably connected to the detector for receiving image data from the detector in response to the operation of the radiation source and processing the image data to form images;

d. an electronic storage device operably connected to the processing device on which instruction for the operation of the processing device can be stored; and e. a medical image data analysis model selection system operably connected to the processing device for performing an automatic selection of a medical image data analysis model for instantiation on the processor, the medical image data analysis model selection system comprising:

i. a server including an electronic storage device including a number of medical image data analysis models stored thereon; and ii. a processor configured to compare extracted features from an evaluation dataset of medical images from the processing device with training features of each of the number of data analysis models, and to provide one or more matched data analysis models for instantiation on the data analysis system, wherein the number of data analysis models are formed by training copies of a global data analysis model at a number of sites using training data at each site to form the number of data analysis models.

18. The medical imaging system of claim 17, wherein the evaluation dataset of medical images from the processing device does not contain annotations.

19. The medical imaging system of claim 17, wherein the processor is configured to provide the training features for the one or more matched data analysis models along with the one or more matched medical image data analysis models for validation of the one or matched medical image data analysis models.

* * * * *